United States Patent [19]

Rocke

[11] Patent Number: 4,564,522
[45] Date of Patent: Jan. 14, 1986

[54] PHARMACEUTICAL PREPARATIONS AND COMPOSITIONS

[75] Inventor: Dennis Rocke, London, England

[73] Assignee: Shelleden Products Limited, London, England

[21] Appl. No.: 525,048

[22] PCT Filed: Nov. 23, 1982

[86] PCT No.: PCT/GB82/00331
§ 371 Date: Jul. 20, 1983
§ 102(e) Date: Jul. 20, 1983

[87] PCT Pub. No.: WO83/01898
PCT Pub. Date: Jun. 9, 1983

[30] Foreign Application Priority Data

Nov. 24, 1981 [GB] United Kingdom ............... 8135311

[51] Int. Cl.[4] .................. A61K 35/78; A61K 31/355; A61K 31/07
[52] U.S. Cl. ............................. 424/195.1; 514/458; 514/725; 514/861; 514/863
[58] Field of Search ..................... 424/195, 284, 344

[56] References Cited

U.S. PATENT DOCUMENTS 3,943,248  3/1976  Shulman .

FOREIGN PATENT DOCUMENTS 1123433  8/1968  United Kingdom .
1453239  10/1976  United Kingdom .

OTHER PUBLICATIONS

Chem. Abst. 9471275v, Refining Peach Oil, 1981.
Modern Drug Encyclopedia, 9th ed., 1963, p. 1420, "Tocophrin Injection".

Primary Examiner—Jerome D. Goldberg
Assistant Examiner—John W. Rollins
Attorney, Agent, or Firm—Walter J. Kreske

[57] ABSTRACT

A pharmaceutical composition characterized in that it comprises
(a) Vitamin A,
(b) one or more tochopherols
(c) an oil of the genus prunus, and
(d) an oil of the genus sesamum;

in that the weight of each of (c) and (d) is between 5 and 75 times the weight of (a); in that the weight of each of (c) and (d) is between 4 and 125 times the weight of (b); and in that the composition has a consistency suitable for topical application.

16 Claims, No Drawings

PHARMACEUTICAL PREPARATIONS AND COMPOSITIONS

TECHNICAL FIELD

This invention relates to pharmaceutical preparations and compositions, particularly but not exclusively for external application to provide symptomatic relief of dermatological conditions, e.g. excema, psoriasis, herpes simplex (cold sores) and the like; and their manufacture.

DISCLOSURE OF INVENTION

According to this invention there is provided a pharmaceutical composition characterised in that it comprises
(a) Vitamin A,
(b) one or more tochopherols
(c) an oil of the genus prunus, and
(d) an oil of the genus sesamum,
in that the weight of each of (c) and (d) is between 5 and 75 times the weight of (a); in that the weight of each of (c) and (d) is between 4 and 125 times the weight of (b); in that the composition has a consistency suitable for topical application in that the genus prunus consists of five members, viz. *prunus communis* (almond), *prunus armeniaca* (apricot), *prunus persica* (peach), *prunus domestica* (plum) and *prunus cerasus* (cherry); and in that the genus sesamum consists of three members, viz. *sesamum indicum, ceratotheca sesamoides* and *sesamum angustifoloum*.

Advantageously the ratio of the weight of (a) to (b) is in the range 1:15.5 to 21:1. Preferably the weight of (a) is between 0.75 and 1.8 times the weight of (b).

Preferably the weights of (a) and (b) are substantially the same.

Preferably the weights of (c) and (d) are substantially the same.

Preferably the weight of (c)—or (d)—is approximately 18 to 19 times the weight of (a) and approximately 20 times the weight of (b).

In preferred examples of this invention, (c) comprises almond oil and (d) comprises sesame seed oil.

Advantageously said preparation or composition further comprises olive oil, the weight of olive oil being preferably between 9 and 140 times the weight of (a) and/or between 7 and 250 times the weight of (b).

Preferably said Vitamin A is in the form of the resin palmitate.

BEST MODE OF CARRYING OUT THE INVENTION

Various preferred embodiments of this invention will now be described, reference being had to Table A.

In all these preferred embodiments of Table A, the Vitamin A employed is in the form of the palmitate resin oil with a strength of $1 \times 10^6$ International Units per gm of the oil. The palmitate Vitamin A alone has a strength of $1.87 \times 10^6$ International Units per gm whence it will be appreciated that the weight figures for constituent (a) in columns I, II, III and IV of Table A corresponds respectively 4–10, 2, 10 and 5 ml of the said palmitate resin oil.

In these preferred embodiments of Table A, the Vitamin E employed constitutes and is provided by a mixture of tochopherols—typically 10–15% alpha-tochopherols, 64–76% of a combination of beta-tochopherols and gamma-tochopherols, and 20–30% delta-tochopherols. For the purposes of these examples, the reference to Vitamin E is to be taken as a reference to the whole mixture of tochopherols employed rather than, for example, to just the alpha-tochopherols (which are considered by some authorities to be the essential substance to which the term Vitamin E may be employed). For the composition of column II of Table A, the Vitamin E employed was in an oil form known as $T_{30}$, i.e. having 300 mg of tochopherols per ml of oil, and the indicated weight of 0.6 g therefore corresponds to 2 ml of the oil $T_{30}$. For the composition of column III of Table, the Vitamin E employed was in an oil form known as $T_{70}$, i.e. having 700 mg of tochopherols per ml of oil, and the indicated weight of 7 g therefore corresponds to 10 ml of the oil $T_{70}$. For the compositions of columns I and IV of Table A, the Vitamin E employed was in an oil form known as $T_{50}$ (e.g. that sold under the Trade Mark "COVIOX $T_{50}$"), i.e. having 500 mg of tochopherols per ml of oil, and the indicated weights of 2–5 g and 2.5 g therefore correspond to respectively 4–10 ml and 5 ml of the oil $T_{50}$.

TABLE A

| | Composition | | | | | | | |
| | I | | II | | III | | IV | |
| Constituent | g | % | g | % | g | % | g | % |
| --- | --- | --- | --- | --- | --- | --- | --- | --- |
| (a) Vitamin A | 2.14–5.35 | 1.56–2.05 | 1.07 | 0.4 | 5.35 | 4.4 | 2.67 | 1.3 |
| (b) Vitamin E | 2–5 | 1.30–1.92 | 0.6 | 0.2 | 7 | 5.7 | 2.5 | 1.2 |
| (c) Almond Oil B.P. | 40–60 | 26.0–23.1 | 70 | 24.0 | 30 | 24.5 | 50 | 24.4 |
| (d) Sesame Seed Oil B.P. | 40–60 | 26.0–23.1 | 70 | 24.0 | 30 | 24.5 | 50 | 24.4 |
| (e) Olive Oil B.P | 70–130 | 45.4–49.9 | 150 | 51.4 | 50 | 40.9 | 100 | 48.7 |

Note: percentage figures shown are approximate

It will be appreciated that in the preferred embodiments of Table A, the almond oil employed is an oil derived from the kernal of a fruit of the genus *prunus amygdalus* variety "AMARA" or *prunus amygdalus* variety "DULCIS", and the sesame seed oil (or sesame oil) employed is an oil derived from the seed of the genus *sesamum indicum* (L. Pedaliaceae).

In forming each of the embodiments of Table A, all the constituents—in oil form—were added to one another at room temperature and mixed well.

The compositions represented by column I of Table A are preparations with preferred ranges of the constituents (a) to (e). The composition of column II of Table A is considered to be a potentially rather weak preparation according to this invention and yet remaining reasonably effective for symptomatic relief of, for example, excema. In contrast, the composition of column III of Table A is considered to be a potentially very strong and effective preparation according to this invention. A particularly preferred preparation according to this invention is the composition set out in column IV of Table A, this composition being currently considered as probably the strongest one which would not be dangerous if taken internally by mistake.

From the approximate percentage figures given in Table A it will be noted that:

constituent (a) varies between 0.37% and 4.37%, and in preferred composition IV is 1.30%, of the total;

constituent (b) varies between 0.21% and 5.72%, and in preferred composition IV is 1.22%, of the total;

each of constituents (c) and (d) varies between 23.1% and 26.0% and in the preferred composition IV each constitute 24.4% of the total;

and consitutent (e) varies between 40.9% and 51.4%, and in preferred composition IV is 48.9%, of the total. From calculations based on these figures it can be determined (i) that the ratio of constituent (c) or (d) to constituent (a) is between 5.3 and 70.3, i.e. within the range 5 to 75 obtained by appropriate rounding up and down, and is preferably 18.8, i.e. about 18 to 19, (ii) that the ratio of constituent (c) or (d) to constituent (b) is between 4.0 and 123.8, i.e. within the range 4 to 125, and is preferably about 20, (iii) that the ratio of constituent (a) to constituent (b) is in the range 0.06:1 to 21:1, i.e. 1:15.5 to 21:1, and is preferably in the range 0.76:1 to 1.81:1, i.e. about 0.75:1 to 1.8:1, (iv) that this last ratio is 1.07 in the case of preferred composition IV, i.e. the weights of constituents (a) and (b) are substantially the same, (v) that the ratio of constituent (e) to constituent (a) is between 9.24 and 138.9, i.e. within the range 9 to 140 obtained by appropriate rounding up and down, and is 37.6 (i.e. about 37) in the case of preferred composition IV, (vi) that the ratio of constituent (e) to constituent (b) is between 7.15 and 244.8, i.e. within the range 7 to 250 obtained by appropriate rounding up and down, and is 40.1 (i.e. about 40) in the case of preferred composition IV.

For topical application the constituents (a) to (e) of each composition may remain in the natural oil-like state obtained by adding them to one another, or they may be emulsified by appropriate emulsifying agents to form a suitable or desired consistency, e.g. of a cream or of an ointment.

In tests and experiments conducted to date by applying composition IV to affected areas of the skin, remarkably positive and beneficial results have been noticed. The preparation has proved fast-acting, effective and long-lasting in alleviating the irritation, itching and burning sensations usually ocurring with dermatological conditions such as excema, psoriasis, athlete's foot, herpes simplex, heat bumps, insect bites and the like, as well as with symptoms occurring with haemorrhoids. Moreover, a definite observed result has been experienced in many instances where the composition appears to accelerate the body's natural healing ability as noted by comparison of treated area healing times R2, R3, R4 and R7 (recorded in TABLE B below) to R8 healing times of untreated lesions. In many cases, symptomatic relief for over 8 hours was enjoyed from a single application of composition IV.

For example, in a pilot study along the lines of a "double blind" trial, the efficiency of composition IV of Table A was tested against (A) cold sores, i.e. herpex simplex labialis, and (B) minor skin irritations.

For test (A), ten volunteers with herpes simplex labialis participated on a random basis. Eight volunteers had two lesions each and acted as their own controls by first applying composition IV to the larger lesion only. In all eight cases composition IV was applied to the smaller lesion after at least one week without any medication thereto. One of the volunteers with only one lesion agreed not to apply any medication at all. Similarly for test (B), ten volunteers with various forms of skin irritations participated on a random basis. All volunteers with eczema or dermatitis agreed to apply composition IV to a marked test area alone for 7 days, thus acting as their own controls. All cases were spontaneous healing of the untreated area occurred within 7 days were discarded. Written, informed consent was obtained from all volunteers or guardians before tests (A) and (B). The sex, age, complaint, treatment and results associated with each volunteer are tabulated in Table B and its accompanying Notes from which it is clear that said composition IV is most efficacious against herpex simplex labialis and minor skin irritations.

TABLE B

| Test | Volunteer Number | Sex | Age | Complaint Number | Treatment No. | Results Treated Lesion or Area | Results Untreated Lesion[1] or Area |
|---|---|---|---|---|---|---|---|
| (A) | 1 | M | 62 | C1 | T1 | R3 | R8 |
| | 2 | F | 27 | C1 | T1 | R3 | R8 |
| | 3 | F | 21 | C1 | T1 | R4 | R8 |
| | 4 | M | 67 | C1 | T1 | R3 | R8 |
| | 5 | F | 18 | C1 | T1 | R3 | R8 |
| | 6 | F | 45 | C1 | T1 | R4 | R8 |
| | 7 | F | 57 | C1 | T1 | R3 | R8 |
| | 8 | F | 44 | C2 | T1 | R3 | R8 |
| | 9 | M | 39 | C2 | T2 | — | R8 |
| | 10 | F | 62 | C2 | T3 | R3 | — |
| (B) | 11 | F | 3 | C3 | T4 | R7 | R8 |
| | 12 | F | 5 | C3 | T4 | R7 | R8 |
| | 13 | F | 54 | C4 | T4 | R2 | R8 |
| | 14 | F | 34 | C4 | T4 | R2 | R8 |
| | 15 | F | 18 | C4 | T4 | R2 | R8 |
| | 16 | F | 2 | C4 | T4 | R2 | R8 |
| | 17 | M | 7 | C4 | T4 | R2 | R8 |
| | 18 | F | 11 | C4 | T4 | R2 | R8 |
| | 19 | M | 24 | C5 | T3 | R4 | — |
| | 20 | F | 25 | C5 | T3 | R3 | — |

Notes

M = Male
F = Female

C1 = 2 herpes simplex lesions
C2 = 1 herpex simplex lesions
C3 = dermatitis
C4 = eczema
C5 = herpangina

[1] All lesions healed within 5 days after treatment with Composition IV (of Table A) initiated.

T1 = Composition IV (of Table A) applied to larger lesion immediately and to smaller lesion after 1 week.
T2 = None
T3 = Composition IV (of Table A) applied to the 1 lesion.
T4 = Composition IV (of Table A) applied to marked test area.

R2 = Healed after 2 days
R3 = Healed after 3 days
R4 = Healed after 4 days
R7 = Healed after 3 days but relapse 4 days after treatment stopped.
R8 = Accute inflamatory changes still present after 8 days.

TABLE C

| Test | Composition | Efficiency against herpex simplex labialis and minor skin irritations |
|---|---|---|
| 1. | IV of TABLE A | Very efficacious, and long-lasting relief. |
| 2. | 2.5 g vitamin E 50 g almond oil 50 g sesame oil 100 g olive oil | very slight efficacy, but of reasonable duration |

TABLE C-continued

| Test | Composition | Efficiency against herpex simplex labialis and minor skin irritations |
| --- | --- | --- |
| 3. | 2.7 g vitamin A<br>50 g almond oil<br>50 g sesame oil<br>100 g olive oil | very slight efficacy, but of reasonable duration. |
| 4. | 2.7 g vitamin A<br>2.5 g vitamin E<br>50 g sesame oil<br>100 g olive oil | only slight relief (of reasonable duration) but some burning sensation. |
| 5. | 2.7 g vitamin A<br>2.5 g vitamin E<br>50 g almond oil<br>100 g olive oil | only slight relief, of short duration, and some burning sensation. |
| 6. | 2.7 g vitamin A<br>2.5 g vitamin E<br>50 g almond oil<br>50 g olive oil | substantial initial relief but insufficiently long-lasting. |

From other experimental tests conducted (see Table C) it appears that all four constituents (a) to (d) are necessary to achieve appreciable relief. Where one of the vitamins (A or E) is omitted from the composition (test 2 or 3 in Table C) the beneficial effects are severly curtailed and only minimal relief is obtained. Omission of either almond oil or sesame seed oil (test 4 or 5 in Table C) causes a similar depreciation of the relief obtainable and leaves just a burning sensation. The trials and experiments clearly show a synergistic effect with all four constituents (a) to (d). The provision of constituent (e), i.e. the olive oil, increases substantially the long-lasting nature of the relief provided by the composition. (see test 6 in Table C).

Although the reason for such a surprising synergistic effect is not known, it is thought possible that, notwithstanding the vegetable-oil-like characteristics of constituents (c), (d) and (e), the composition as a whole could act as an inhibitor of the lipoxygenase enzyme to inhibit production of inflammatory leukotrienes, i.e. the lipoxygenase metabolits of arachidonic acid (which are generally found in vegetable oils), and which are thought to cause psoriasis and kindred dermatological disorders.

According to another aspect of this invention there is provided a method of manufacturing a pharmaceutical composition, said method being characterised in that it comprises admixing to one another:
(a) Vitamin A,
(b) one or more tochopherols
(c) an oil of the genus prunus, and
(d) an oil of the genus sesamum;
in that the weight of each of (c) and (d) is between 5 and 75 times the weight of (a); in that the weight of each of (c) and (d) is between 4 and 125 times the weight of (b); and in that the composition has a consistency suitable for topical application.

INDUSTRIAL APPLICABILITY

From the foregoing it will be appreciated that this invention is capable of widespread exploitation in the pharmaceutical and ethical chemical industry, and in medicine.

What is claimed is:

1. A pharmaceutical composition characterised in that it comprises
(a) Vitamin A,
(b) at least one tochopherol
(c) an oil of the genus prunus, and
(d) an oil of the genus sesamum
in that the weight of each of (c) and (d) is between 5 and 75 times the weight of (a); in that the weight of each of (c) and (d) is between 4 and 125 times the weight of (b); and in that the composition has a consistency suitable for topical application.

2. A pharmaceutical composition according to claim 1, characterised in that the ratio of the weight of constituent (a) to constituent (b) is within the range 1:15.5 to 21:1.

3. A pharmaceutical composition according to claim 1, characterised in that the weight of constituent (a) is between 0.75 and 1.8 times the weight of constituent (b).

4. A pharmaceutical composition according to claim 1, characterised in that the weight of constituents (c) and (d) are substantially the same.

5. A pharmaceutical composition according to claim 1, characterised in that the weights of constituents (a) and (b) are substantially the same.

6. A pharmaceutical composition according to claim 1, characterised in that the weight of constituent (c) is substanitally the same as the weight of constituent (d) and is approximately 18 to 19 times the weight of consituent (a), and approximately 20 times the weight of constituent (b).

7. A pharmaceutical composition according to claim 1, characterised in that constituent (c) comprises almond oil.

8. A pharmaceutical composition according to claim 1, characterised in that constituent (d) comprises sesame seed oil of the species indicum.

9. A pharmaceutical composition according to claim 1, characterised in that it further comprises olive oil.

10. A pharmaceutical composition according to claim 1, characterised in that said Vitamin A is in the form of the resin palmitate.

11. A pharmaceutical composition according to claim 9, characterised in that the weight of olive oil is between 9 and 140 times the weight of constituent (a).

12. A pharmaceutical composition according to claim 9, wherein the weight of olive oil is between 7 and 250 times the weight of constituent (b).

13. A pharmaceutical composition according to claim 9, characterised in that the weight of olive oil is approximately 37 to 40 times the weight of each of the constituents (a) and (b).

14. A pharmaceutical composition characterised in that it comprises
(a) 1.0 to 5.4 parts by weight Vitamin A
(b) 0.6 to 7.0 parts by weight Vitamin E
(c) 30 to 70 parts by weight Almond Oil
(d) 30 to 70 parts by weight Sesame Seed Oil, and
(e) 50 to 150 parts by weight Olive Oil;
in that the weight of each of (c) and (d) is between 5 and 75 times the weight of (a); in that the weight of each of (c) and (d) is between 4 and 125 times the weight of (b); and in that the composition has a consistency suitable for topical application.

15. A pharmaceutical composition according to claim 14, characterised in that it comprises
(a) 2.7 parts by weight Vitamin A
(b) 2.5 parts by weight Vitamin E
(c) 50 parts by weight Almond Oil
(d) 50 parts by weight Sesame Seed Oil
(e) 100 parts by weight Olive Oil.

16. A pharmaceutical composition according to claim 15, characterised in that said Vitamin A is in the form of the resin palmitate.

* * * * *